United States Patent [19]

Platt

[11] Patent Number: 5,776,069

[45] Date of Patent: Jul. 7, 1998

[54] METHOD AND SYSTEM FOR QUANTITATIVELY DETERMINING EKG WAVEFORM ORGANIZATION

[75] Inventor: John S. Platt, Corvallis, Oreg.

[73] Assignee: Hewlett-Packard Company, Palo Alto, Calif.

[21] Appl. No.: 781,115

[22] Filed: Jan. 9, 1997

[51] Int. Cl.[6] .................................................. A61B 5/0472
[52] U.S. Cl. ............................................................. 600/515
[58] Field of Search .......................... 600/509, 515–518, 600/521

[56] References Cited

U.S. PATENT DOCUMENTS

| | | | |
|---|---|---|---|
| 4,742,458 | 5/1988 | Nathans et al. | 600/516 |
| 5,447,519 | 9/1995 | Peterson | 600/518 |
| 5,509,425 | 4/1996 | Feng | 600/515 |
| 5,634,468 | 6/1997 | Platt et al. | 600/509 |

*Primary Examiner*—Jeffrey R. Jastrzab

[57] ABSTRACT

A method and system for assessing the regularity of heart function, to be utilized with electrocardiographic (hereinafter "EKG") waveform representations of heart function. The method and system work by first monitoring and recording a particular patient's EKG waveform data for a defined period of time. As the EKG waveform data is being monitored and recorded, a set of EKG waveforms is created from the monitored and recorded data. The set is made up of waveforms deemed to be dissimilar. After the defined period of time has elapsed, the total number of dissimilar waveforms in the set are counted, and the total count of the dissimilar waveforms in the set is divided by total number of waveforms that were contained within the EKG data recorded and monitored during the defined period of time. The result of this division is deemed the disorganization index, and serves as a measure of how dissimilar succeeding waves in the EKG wavetrain data were, and thus gives a good indication of the regularity of heart function.

6 Claims, 2 Drawing Sheets

METHOD AND SYSTEM FOR QUANTITATIVELY DETERMINING EKG WAVEFORM ORGANIZATION

BACKGROUND

1. Technical Field:

The present invention relates, in general, to improved heart monitoring equipment to be utilized in monitoring electrocardiographic waveform data and, in particular, to improved heart monitoring equipment to be utilized in monitoring electrocardiographic waveform data and which can assess the regularity of heart function. Still more particularly, the present invention relates to improved heart monitoring equipment to be utilized in monitoring electrocardiographic waveform data and which can assess the regularity of heart function by utilizing information contained within multiple heart beat patterns of a patient's electrocardiographic waveform data. Yet still more particularly, the present invention relates to improved heart monitoring equipment to be utilized in monitoring electrocardiographic waveform data and which can assess the regularity of heart function by utilizing information contained within multiple heart beat patterns of a patient's electrocardiographic waveform data such that the advisability of defibrillation can be more accurately determined.

2. Description of Related Art:

The present invention remedies a deficiency of the prior art methods and systems for assessing the regularity of heart function on the basis of electrocardiographic waveform data. The deficiency remedied is the inability of the prior art methods and systems to detect irregularity of heart function when such irregularity manifests itself as relatively severe morphological changes in electrocardiographic waveforms when such changes are the result of an aggregate of gradual beat-to-beat changes in waveform morphology spanning several heartbeats. In other words, the prior art is incapable of detecting irregularity of heart function when such irregularity manifests itself as a gradual degradation of the successive heartbeat electrocardiographic waveforms when such degradation occurs over the course of several heartbeats.

The deficiency of the prior art remedied by the present invention arises from the fact that the prior art has utilized communications engineering techniques (e.g., autocorrelation ) in an attempt to assess the regularity of heart function. The problem with this approach is that communications engineering techniques are designed for use in the non-biological sciences where reproducibility and repeatability of phenomena are the norms (e.g., the "laws" of nature, or the fact that a sine wave in one lab is virtually the same as a sine wave in any other lab), while the electrocardiographic data to which the techniques are being applied arise from biological science where individuality and irreproducibility are the norms (e.g. fingerprints, retinal scans, faces). As one would expect, applying such non-biological techniques to biological data yields only mediocre results, and such application is generally only able to detect irregularity of heart function which manifests itself as severe changes contained within a small number of successive electrocardiographic waveforms (e.g., when the heart goes from a periodic beat into chaotic fibrillation, relatively quickly).

The present invention remedies the deficiency of the prior art by completely turning away from the way heart function was assessed in the past, and instead employing a completely new technique. In the present invention, each patient's individual electrocardiographic waveform data (which is composed of successive electrocardiographic waveforms) is made the standard by which the regularity of that patient's heart function is evaluated. Rather than use autocorrelation techniques, the present invention observes and "remembers" what the patient's successive electrocardiographic waveforms "look like" (preferably by creating waveform templates). If the invention determines that a successive waveform does not "look like" any earlier waveform, this fact is so noted and a count is kept of the number of waveforms which do not "look like" other waveforms. By doing this, the present invention is able to give a running assessment as to how regular or irregular the patient's heart function is by comparing the count of the number of waveforms that did not "look like" other waveforms with the total number of waveforms.

In the following discussion of both the prior art and the present invention, it is helpful to have a basic understanding of the electrocardiograph, since both the prior art and the present invention utilize electrocardiographic waveform data in order to assess the regularity of heart function. Accordingly, as an aid to understanding the electrocardiograph, the discussion below presents a brief description of (1) the electrochemical and mechanical operation of the heart, and (2) how the electrochemical operation of the heart is transduced into electrical energy which is then used by the electrocardiograph to graphically denote the mechanical operation of the heart.

The heart is generally described as being composed of four chambers: the right atrium, the right ventricle, the left atrium, and the left ventricle. There is a one-way valve between the right atrium and the right ventricle (the tricuspid valve). There is a one-way valve between the right ventricle and the arterial system which perfuses the lungs (the pulmonic valve). There is a one-way valve between the left atrium and the left ventricle (the mitral valve). And, lastly, there is a one-way valve between the left ventricle and the aorta (the aortic valve).

In terms of its functional operation, the heart receives oxygen-depleted blood via the vena cavae (the two large veins which return blood to the heart). These large veins empty into the right atrium. The right atrium then pushes this oxygen-depleted blood into the right ventricle. Next, the right ventricle pushes this oxygen-depleted blood into one long, continuous fluid path composed of, in sequence, the pulmonary artery, the capillary beds perfusing the lungs, and the pulmonary veins which empty into the left atrium. The continuous path ends with the left atrium, which is to say that there is no valve between the pulmonary veins and left atrium. Next, the oxygen-rich blood which has entered the left atrium is pushed into the left ventricle. Finally, the left ventricle pushes the blood out into the aorta.

The functional operation, described above, is effectuated by the electrochemical and mechanical operation of the heart as follows. The natural pacemaker of the heart, the sinoatrial nerve, discharges an electrochemical pulse, or action potential, and from this action potential all subsequent electrochemical and mechanical activity of the heart ensues. The sinoatrial nerve is located very near the right atrium, so the initial action potential reaches it almost immediately; simultaneously, the action potential propagates along a very fast conduction internodal tract to the left atrium, with the net result being that the atria (plural of atrium) receive the pulse almost simultaneously. Due to the anatomical structure of the heart, the atria initially receive the pulse upstream from the atrioventricular valves which separate the atria from the ventricles. When the pulse is received, the muscle fibers excited first contract first; in practice, what this means is that the atria of the region upstream contract first, so that the blood is pushed in the downstream direction. This operation is greatly analogous to the way in which toothpaste can be most efficiently squeezed out of the tube by squeezing at the closed end of the tube first.

Although, at this point, the atria have received the action potential, it (the action potential) is continuing to propagate throughout the heart. Simultaneous with the just-described actions involving the atria, the action potential is proceeding over three parallel internodal tracts to the atrioventricular node. The atrioventricular node functions as an analog delay; this delay provides time for atrial contraction to occur (the atria contract with more force over time as more fibers are recruited into contraction), which will enhance the functioning of the atria. After the delayed action potential leaves the atrioventricular nerve, it is conducted along a neural structure known as the bundle of His. Subsequent to this, the neural structure splits and the action potential is conducted by the right and left bundle branches to the regions of the right and left ventricles. Once the action potential arrives at the regions of the right and left ventricles, the action potential activates the Purkinje fibers, which are very fast conduction fibers that conduct the action potential very rapidly over and throughout the ventricles.

Once the ventricles are energized (depolarized), they begin to contract. The ventricles are much stronger and contract more rapidly than the atria (which are, at this point, continuing to contract). Very quickly, the pressure in the ventricular chambers outstrips that of the atria, causing both the mitral and the tricuspid valves to slam shut (because the pressure on the upstream side of these one-way valves exceeds the pressure on the downstream side). Once the right ventricle has outstripped the pressure of the contracting left atrium, the pulmonic valve opens and blood is pumped into the fluid path consisting of the pulmonic artery, capillary bed, pulmonary vein, and left atrium. Subsequent to this, once the left ventricle has outstripped the pressure of the aorta, the aortic valve opens and blood is pushed into the aorta. Once the ventricles have ejected the majority of their contents, the ventricles begin to relax and both the pulmonic and aortic valves close, with the pulmonic valve generally closing first due to the proximity of the continuing-to-contract left atrium.

Once the pressure in the relaxing ventricles falls below that of the continuing-to-contract atria, the atrioventricular valves (tricuspid and mitral) open and the atria push blood into the ventricles. Once the atria have completed this task, they relax and the heart enters a wait state after which the whole foregoing-described process is reinitiated by the next sinoatrial pulse.

As has just been discussed, the mechanical events of the heart are preceded and initiated by the electrochemical activity of the heart (i.e., the propagation of the action potential). There is a device which transforms the electrochemical activity of the heart into a form visible to the human eye: the electrocardiograph, which produces a visual representation of the electrochemical activity of the heart. The visual representation is known as the electrocardiogram ("EKG").

During an EKG, electrodes are attached to the body surface. The electrodes are specially treated to allow the charge carrier within the electrodes (electrons) to communicate with the charge carriers within the body (ions) via electrochemical exchange. Attaching electrodes to the body surface allows the voltage changes within the body to be recorded after adequate amplification of the signal. A galvanometer within the EKG machine is used as a recording device. Galvanometers record potential differences between two electrodes. The EKG is merely the recording of differences in voltage between two electrodes on the body surface as a function of time, and is usually recorded on a strip chart. When the heart is at rest, diastole, the cardiac cells are polarized and no charge movement is taking place. Consequently, the galvanometers of the EKG do not record any deflection. However, when the heart begins to propagate an action potential, the galvanometer will deflect since an electrode underneath which depolarization has occurred will record a potential difference from a region on the body under which the heart has not yet depolarized.

A complete heart cycle is known as a heartbeat. On an EKG, a normal heartbeat has a distinctive signal. Initially, the galvanometer notes a relatively short duration rounded positive deflection (known as the P wave), which is believed to be caused by atrial depolarization. Subsequent to this, there is a small but sharp negative deflection (known as the Q wave). Next, there is a very large and sharp positive deflection (known as the R wave), after which there is a sharp and large negative deflection (known as the S wave). When these waves are taken together, they are known as the QRS complex. The QRS complex is believed to be caused by ventricular depolarization. Subsequent to the QRS complex is a relatively long duration rounded positive deflection (known as the T wave), which is believed to be caused by ventricular repolarization.

Over the years, health care professionals have built up a body of knowledge wherein they have learned to coordinate variations in and data from the EKG with different diseases and heart defects. Formally, this process of coordinating is known as "electrocardiography."

Within electrocardiography, EKG data serve many purposes. One of the purposes served is determining the regularity of heart function; for example, whether or not the heart is following a normal predictable rhythm, or has instead fallen into a non-rhythmic condition indicative of the need for treatment. The problem with electrocardiography is that it is mostly a visual art, meaning that a healthcare professional generally looks at an EKG Strip, notes the changes in waveforms over time (i.e. changes in the QRS waves), and makes an assessment as to the regularity of heart functions. Automating the electrocardiologist's assessment regarding the regularity or irregularity of heart function on the basis of EKG data has proven quite difficult. The prior art solution to the problem has been to try to use communications engineering techniques (specifically, autocorrelation and related techniques) to try to determine if the heart is beating normally. In an autocorrelation detector, a received signal is first duplicated a number of times. Each of the duplicates is then delayed by some differing increment of time. The delayed duplicates are then multiplied by the nondelayed received signal and the result of each such multiplication integrated with respect to time, over some specified period of time.

Autocorrelation can thus do two things: (1) for waveforms that retain some degree of periodicity, give an approximation as to how quickly the function changes with time; and (2) give an indication as to the randomness of the waveform being autocorrelated, since a near random waveform will have a nearly zero autocorrelation. For a quickly changing periodic signal, even a small time delay of the duplicate will result in a relatively small output of an autocorrelation detector (e.g., a 60 hertz sine wave delayed by $\frac{1}{240}$ seconds (or ¼ its period) and autocorrelated will yield a greatly decreased output than that for the same waveform delayed 1/24000 seconds). Conversely, for a slowly changing periodic signal even a large time delay on the duplicate signal will give a relatively large output from a correlation detector (e.g., a 1 hertz sine wave delayed by 1/240 seconds and autocorrelated would result in a very small decrease in the output of an autocorrelation detector). Since in practice many duplicates are created, each with varying levels of delay, and then autocorrelated with the undelayed waveform, the differences in the output of the different autocorrelation operations serves to give an idea as to how quickly the signal is changing. With respect to autocorrelation being able to assess the randomness of the waveform being correlated, the idea is that a random waveform is so chaotic that any autocorrelation will approach zero because the sum of the positive areas will cancel with the sum of the negative areas (such areas being the result of integrating the product of the delayed and undelayed waveforms over a succession of time increments) irrespective of either the time period of integration or the magnitude of the time delay of the delayed waveform.

In practical terms, this means that autocorrelation and similar techniques used in the previous art only work in relation to conditions where the waveforms of the heart change rapidly—that is, where the information of importance is that arising from one beat to the next. For example, in the case where the heart goes from a normal beat into fibrillation (that is, from a relatively slowly varying waveform to a chaotic white-noise type of signal) autocorrelation can yield detection of the condition because autocorrelating this random waveform will result in near-zero output from an autocorrelation detector. Furthermore, if the heartbeat is radically changing from one beat to the next in either time or shape, the detector might work (how well it would work would depend upon the degree of the shape change and how rapidly the changes are taking place).

Thus, the above discussion demonstrates that a major drawback of autocorrelation is that it tends to be more sensitive to regularity of the waveform in the time domain and less sensitive to waveforms of constantly changing morphology such as are typically present in ventricular fibrillation and such polymorphic tachycardias as "Torsade de Points." These two arrhythmias may in fact appear quite regular in the time domain as they are known to be fairly narrow band signals. What is needed is a method which is more sensitive to variations in the morphology of EKG cycles.

From the foregoing discussion it is apparent that a need exists for the present invention: a method and system which can assess the regularity of heart function on the basis of information contained within multiple heart beat patterns of a patient's EKG waveform data, even when such EKG waveform data will demonstrate reasonably good autocorrelation.

SUMMARY OF THE INVENTION

It is therefore one object of the present invention to provide improved heart monitoring equipment to be utilized in monitoring EKG waveform data.

It is another object of the present invention to provide improved heart monitoring equipment to be utilized in monitoring EKG waveform data and which can assess the regularity of heart function.

It is yet another object of the present invention to provide improved heart monitoring equipment to be utilized in monitoring EKG waveform data and which can assess the regularity of heart function by utilizing information contained within multiple heart beat patterns of a patient's EKG waveform data.

It is yet still another object of the present invention to provide improved heart monitoring equipment to be utilized in monitoring electrocardiographic waveform data and which can assess the regularity of heart function by utilizing information contained within multiple heart beat patterns of a patient's electrocardiographic waveform data such that the advisability of defibrillation can be more accurately determined.

The foregoing objects are achieved as is now described. The improved heart monitoring equipment's method and system work by first monitoring and recording a particular patient's EKG waveform data for a defined period of time. As the EKG waveform data is being monitored and recorded, a set of EKG waveforms is created from the monitored and recorded data. The set is made up of waveforms deemed to be dissimilar. After the defined period of time has elapsed, the total number of dissimilar waveforms in the set are counted, and the total count of the dissimilar waveforms in the set is divided by the total number of waveforms that were contained within the EKG data recorded and monitored during the defined period of time. The result of this division is deemed the disorganization index, and serves as a measure of how dissimilar succeeding waves in the EKG wavetrain data were, and thus gives a good indication of the regularity of heart function.

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION OF PREFERRED EMBODIMENT

Figure 1:
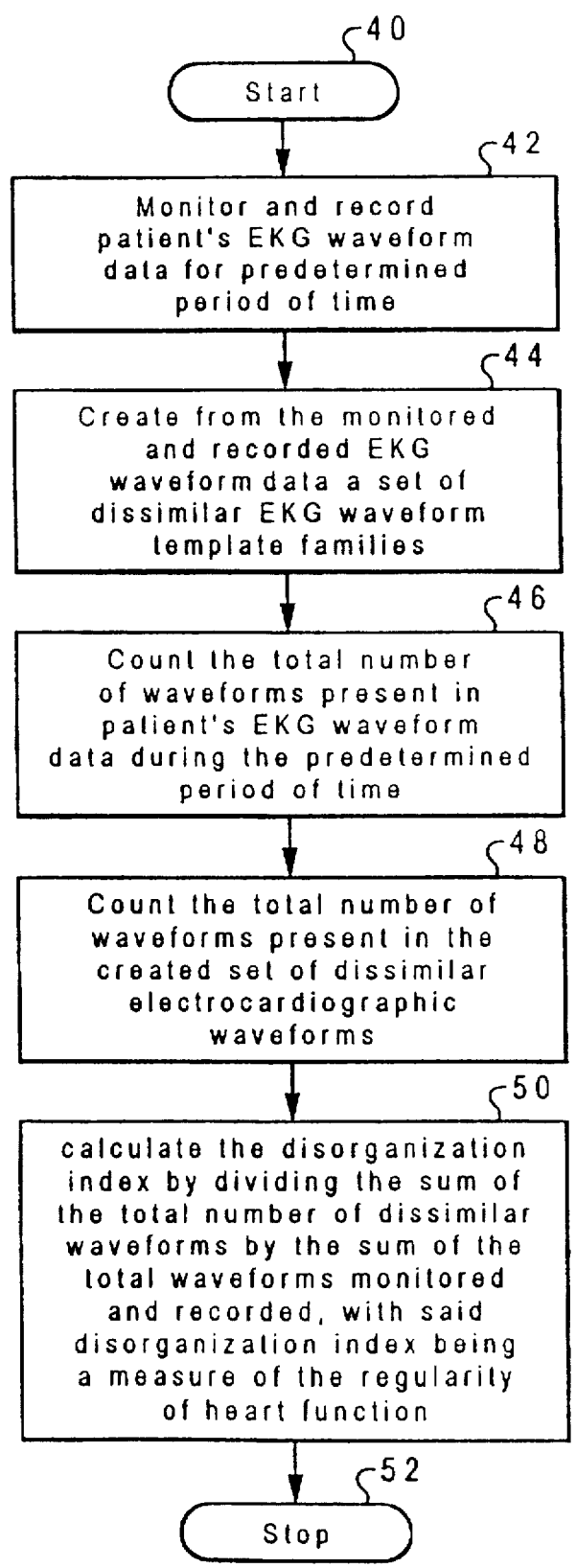
FIG. 1 is a high-level logic flowchart depicting the method and process whereby the present invention assesses the regularity of an individual patient's heart function.

With reference now to the figures and in particular with reference now to FIG. 1, it can be seen that FIG. 1 is a high level logic flowchart depicting the method and process whereby the present invention assesses the regularity of an individual patient's heart function. Method step 40 depicts the beginning of the process. Method step 42 depicts the monitoring and recording of a patient's EKG waveform data for some predetermined period of time. In this method step 42 the waveform is screened for artifacts and any artifacts detected are removed prior to passing the waveform on. The period during which the EKG waveform data will be monitored and recorded is a parameter to be specified either by the operator of the device, or by some certain prestored program, and can range from seconds to minutes.

Method step 44 illustrates the creation of a set of dissimilar EKG waveforms. This set is created by comparing each successive waveform of the patient's EKG waveform data with each waveform in a previously stored data set, and if the waveform compared is dissimilar to all previously stored waveforms, then that waveform is placed into or incorporated within the set of prestored data waveforms. Initially, at the beginning of the process, the prestored data set is empty; that is, it contains no waveforms. However, upon the appearance of the first waveform in the EKG data, that first waveform is stored in the set of previously stored waveforms. Next, the subsequent waveform in the patient's EKG data is compared to this first previously stored waveform. And if the comparison indicates that the waveforms are dissimilar, then that second waveform is stored in the set of previously stored EKG waveforms, but otherwise that second waveform is not stored in the set of previously stored waveforms.

The creation of a set of dissimilar waveforms shown in method step 44 is based upon a concept of waveform "families." A "family" of waveforms is deemed to be some base waveform plus some variations about that base EKG waveform template. The qualities which could vary are numerous, but in the preferred embodiment the waveform templates are compared on a sample-by-sample basis using the normalized mean absolute difference as the measure of dissimilarity.

This mean absolute difference is computed by summing the absolute differences between mean-centered waveforms across a sample window and then dividing by the cumulative sum over both waveforms to normalize for amplitude. Those templates whose measure of dissimilarity falls below an experimentally determined threshold are considered to form a single family.

In the preferred embodiment, it is important to experimentally determine the optimal level for the similarity measure such that the algorithm has the best performance for distinguishing between organized and disorganized rhythms for the application for which it was designed. The optimal level can be determined by plotting the number of templates generated for a given number of beats as a function of the similarity measure threshold. This can be done for a set of prototypical organized and disorganized rhythms. The optimal threshold can then be determined by finding the point of maximum separation between the resulting curves for organized and disorganized rhythms.

Furthermore, in the preferred embodiment it is important to be able to prevent the formation of "families" from artifacts, or spurious signals, which may be similar to one another but which do not represent real EKG waveforms. For this purpose, for each family template formed, waveform features are extracted such as amplitude, width, polarity, etc. These features are examined in order to determine whether a given family represents a valid QRS complex. Families whose features fail to lie within reasonable bounds are discarded and the total beat count is also reduced correspondingly.

On the basis of the waveform variations, whether measured by the means of the preferred embodiment or by other methods, a determination is made as to whether each successive waveform processed either falls within one of the second EKG waveform "families" or, instead, is sufficiently different from the previously received waveforms such that it mandates the creation of a new "family." Thus, the creation of a set of dissimilar waveforms may be described as the creation of a set of "families" of waveforms.

Method step 46 depicts the counting of the total number of waveforms present in the segment of the patient's EKG waveform data that was monitored and recorded during the predetermined period of time referred to in method step 42. That is, upon the expiration of the predetermined period of time, the total number of EKG waveforms that was monitored and recorded during that period of time are counted up and stored. For example, it could be twenty waveforms that were observed and recorded, or thirty waveforms, or forty waveforms, etc.

Method step 48 illustrates the counting of the total number of waveforms present in the set of dissimilar waveforms created in method step 44. That is, method step 48 depicts the counting of the total number of waveform template "families" that were created from the patient's EKG waveform data which was monitored and recorded during the predetermined period of time of method step 42.

Method step 50 depicts the calculation of a disorganization index. This disorganization index is calculated by dividing the counted total number of dissimilar waveforms in the set created in method step 44 by the total number of waveforms counted in method step 46. It is understood that both the waveforms in the set of dissimilar waveforms and the waveforms monitored and recorded are those that occurred during the predetermined period of time of method step 42. As stated, the disorganization index is a quantity obtained by dividing the total number of dissimilar waveforms in the patient's EKG data by the total number of waveforms actually received. Thus, if every single waveform in a patient's EKG data was similar to the point that only one "family" of waveforms was created, the disorganization index would be low since you would have one divided by the total number of waveforms received during the predetermined period of time of method step 42. On the other hand, if the heart was producing waveforms such that every successive wave was different, then the total number of waveforms in the set of dissimilar waveforms would be equal or virtually equal to the number of waveforms received, and thus the disorganization index would be high. Thus, the disorganization index functions as an indicator of the regularity of heart function.

Method step 52 depicts the end step of the method wherein the present invention assesses the regularity of heart function.

Figure 2:
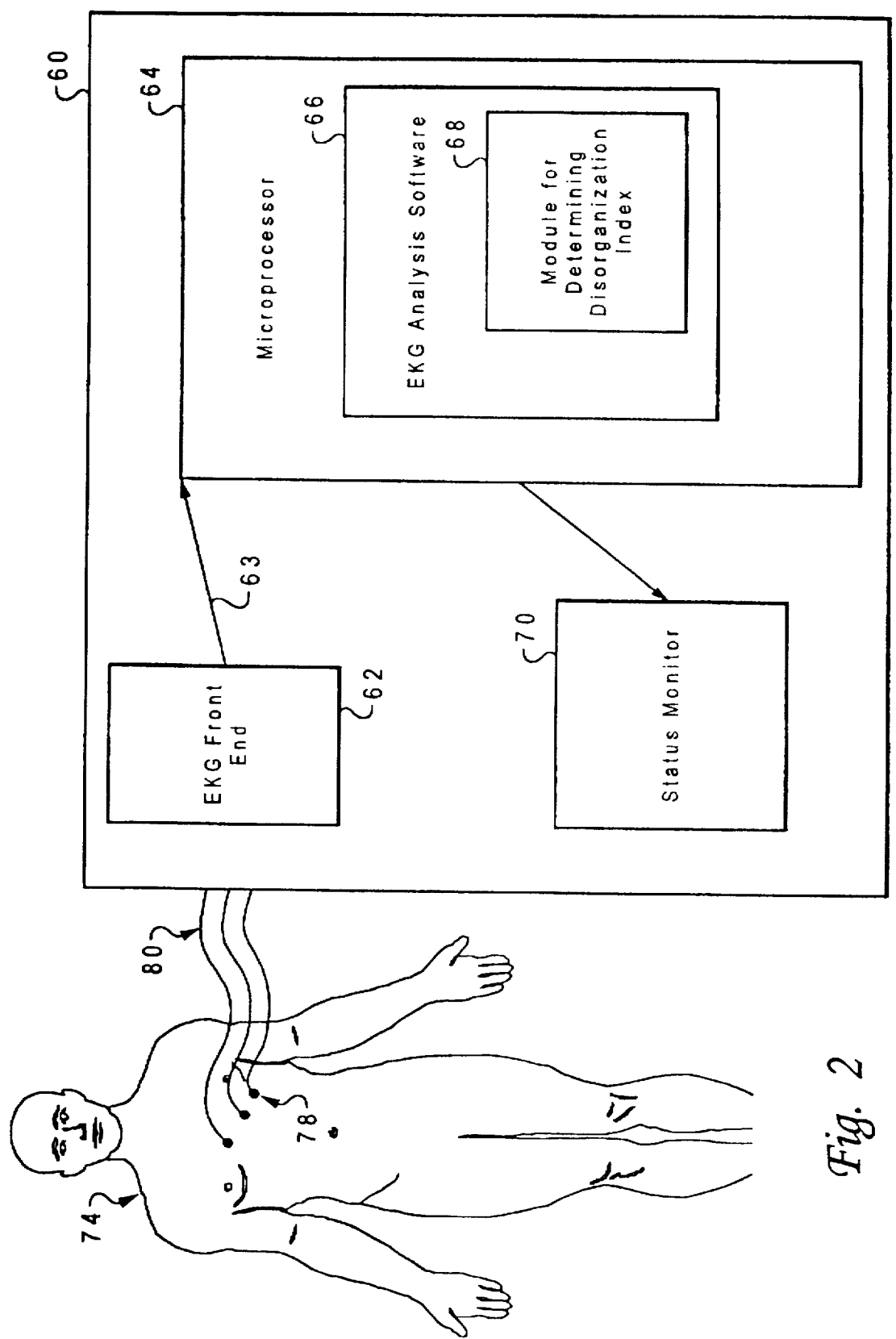
FIG. 2 illustrates a high-level schematic view of a system for implementing the present invention.

Referring now to FIG. 2, there is depicted a high level schematic view of a system for implementing the present invention. FIG. 2 presents the system as a set of programs running on computer machinery, but those skilled in the art will recognize that the functions described here as software could be implemented in hardware or firmware. FIG. 2 depicts a person 74 to whom a number of electrocardiographic ("EKG") electrodes 78 are attached. The electrodes connect via conducting lines 80 to EKG monitor 60. EKG monitor 60 produces EKG waveform signals which are then fed to EKG front end 62. EKG front end 62 signal conditions and filters the EKG waveform signals and then A/D converts and outputs a stream of discretely sampled EKG waveforms, which for simplicity of understanding will simply be referred to as stream of EKG waveforms 63.

Stream of EKG waveforms 63 is delivered to microprocessor 64 which is running EKG analysis software 66, within which is contained module for determining disorganization index 68. Module for determining disorganization index 68 contains programming sufficient to execute the flowchart of FIG. 1. The result of executing the flowchart of FIG. 1 is a disorganization index. EKG analysis software 66 contains programming sufficient to utilize this disorganization index together with other features extracted from the EKG signal, to drive decision logic resulting in a message to the user of EKG monitor 60 indicating whether a defibrillation shock is advised or not.

EKG analysis software 66 can also contain programming sufficient to utilize this disorganization index to determine the regularity of heart function and to output both the calculated disorganization index and assessed regularity of heart function to status monitor 70, which displays the disorganization index and assessed regularity of heart function, and which may be a visual display, audio display, or some combination of both; furthermore, status monitor 70 could possibly include a tactile device (e.g., a vibrating pager) which could be used in addition to audio and visual devices to alert personnel when the disorganization index indicates a critical condition exists.

While an illustrative embodiment has been particularly shown and described, it will be understood by those skilled in the art that various changes in form and detail may be made therein without departing from the spirit and scope of the illustrative embodiment.

What is claimed is:

1. A method for assessing the regularity of heart function, to be utilized with electrocardiographic waveform representations of heart function, said method comprising the steps of:

monitoring and recording a patient's electrocardiographic waveform data for a predetermined period of time;

creating, from said patient's monitored and recorded electrocardiographic waveform data a set of dissimilar electrocardiographic waveforms; and calculating a disorganization index on the basis of said set of dissimilar waveforms and said monitored and recorded electrocardiographic waveform data such that the regularity of said patient's heart function is assessed on the basis of said disorganization index.

2. The method of claim 1, wherein said step of creating a set of dissimilar electrocardiographic waveforms further comprises the steps of:

comparing each waveform of said patient's monitored and recorded electrocardiographic waveform data with each waveform in a previously stored set of dissimilar EKG waveforms; and in response to said comparison, adding to said previously stored set of dissimilar electrocardiographic waveforms each electrocardiographic waveform from said patient's monitored and recorded electrocardiographic waveform data that fails to approximately match any EKG waveform in said previously stored set of dissimilar EKG waveforms.

3. The method of claim 1, wherein said step of calculating a disorganization index further comprises the steps of:

summing the total number of waveforms in said created set of dissimilar electrocardiographic waveforms;

summing the total number of individual waveforms in said patient's monitored and recorded electrocardiographic waveform data; and dividing said sum of the total number of waveforms in said created set of dissimilar electrocardiographic waveforms by said sum of the total number of individual waveforms in said patient's monitored and recorded waveforms and designating the result of said division to be said disorganization index.

4. A system for assessing the regularity of heart function, to be utilized with electrocardiographic waveform representations of heart function, said system comprising:

means for monitoring and recording a patient's electrocardiographic waveform data for a predetermined period of time;

means for creating from said patient's monitored and recorded electrocardiographic waveform data a set of dissimilar electrocardiographic waveforms; and means for calculating a disorganization index on the basis of said set of dissimilar waveforms and said monitored and recorded electrocardiographic waveform data such that the regularity of said patient's heart function is assessed on the basis of said disorganization index.

5. The system of claim 4, wherein said means for creating a set of dissimilar electrocardiographic waveforms further comprises:

means for comparing each waveform of said patient's monitored and recorded electrocardiographic waveform data with each waveform in a previously stored set of dissimilar EKG waveforms; and means for adding, in response to said comparison, to said previously stored set of dissimilar electrocardiographic waveforms each electrocardiography waveform from said patient's monitored and recorded electrocardiography waveform data that fails to approximately match any EKG waveform in said previously stored set of dissimilar EKG waveforms.

6. The system of claim 4, wherein said means for calculating a disorganization index further comprises:

means for summing the total number of waveforms in said created set of dissimilar electrocardiographic waveforms;

means for summing the total number of individual waveforms in said patient's monitored and recorded electrocardiographic waveform data; and means for dividing said sum of the total number of waveforms in said created set of dissimilar electrocardiographic waveforms by said sum of the total number of individual waveforms in said patient's monitored and recorded waveforms and designating the result of said division to be said disorganization index.

* * * * *